(12) United States Patent
Duncan et al.

(10) Patent No.: US 9,820,780 B2
(45) Date of Patent: Nov. 21, 2017

(54) ANGLED OFFSET TULIP ASSEMBLY

(71) Applicant: Amendia, Inc., Marietta, GA (US)

(72) Inventors: Jim Duncan, Hernando, MS (US);
Daniel Sayger, Southaven, MS (US);
Kenneth Richard Barra, Acworth, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 14/871,267

(22) Filed: Sep. 30, 2015

(65) Prior Publication Data

US 2017/0086885 A1 Mar. 30, 2017

(51) Int. Cl.
*A61B 17/70* (2006.01)
*A61B 17/00* (2006.01)

(52) U.S. Cl.
CPC ...... *A61B 17/7032* (2013.01); *A61B 17/7035* (2013.01); *A61B 2017/00526* (2013.01)

(58) Field of Classification Search
CPC ............ A61B 17/7032; A61B 17/7035; A61B 17/7041
See application file for complete search history.

(56) References Cited

U.S. PATENT DOCUMENTS

| | | | |
|---|---|---|---|
| 5,312,404 A | 5/1994 | Asher et al. | |
| 5,344,422 A | 9/1994 | Frigg | |
| 5,879,350 A * | 3/1999 | Sherman | A61B 17/7037 606/266 |
| 6,146,383 A | 11/2000 | Studer et al. | |
| 6,187,005 B1 * | 2/2001 | Brace | A61B 17/7035 606/264 |
| 6,309,390 B1 | 10/2001 | LeCouedic et al. | |
| 6,755,830 B2 | 6/2004 | Minfelde et al. | |
| 7,575,587 B2 | 8/2009 | Rezach et al. | |
| 7,591,838 B2 | 9/2009 | Kramer et al. | |
| 7,704,270 B2 | 4/2010 | DeConinck | |
| 8,062,339 B2 | 11/2011 | Hammer et al. | |
| 8,361,120 B2 | 1/2013 | Gabelberger et al. | |
| 8,435,267 B2 | 5/2013 | Chin et al. | |
| 2006/0036252 A1 * | 2/2006 | Baynham | A61B 17/7035 606/308 |
| 2007/0288004 A1 * | 12/2007 | Alvarez | A61B 17/7032 606/86 A |
| 2009/0036929 A1 * | 2/2009 | Reglos | A61B 17/7035 606/278 |
| 2011/0034955 A2 | 2/2011 | Laager et al. | |
| 2012/0150239 A1 * | 6/2012 | Garamszegi | A61B 17/7032 606/328 |

(Continued)

*Primary Examiner* — Julianna N Harvey
(74) *Attorney, Agent, or Firm* — David L. King (57) ABSTRACT

An angled offset tulip has an angled offset tulip with a rod receiving portion and a bone screw receiving portion. The bone screw receiving portion has a distal opening on a distal end. The rod receiving portion is positioned offset a distance from a center of the distal opening and elevated above the distal opening to form an angle θ. The angle θ is defined as a line passing through the center of the distal opening and a slotted end center. The rod receiving portion has a slotted opening defined by a pair of sides, each side having a proximal end with threads for engaging a set screw to secure a rod. The angled offset tulip can be an angled offset tulip assembly having a collet for receiving, holding and fixing the head of a bone screw.

19 Claims, 9 Drawing Sheets

(56) References Cited

U.S. PATENT DOCUMENTS

2012/0221055 A1    8/2012  Copf
2013/0072991 A1    3/2013  Rathbun
2015/0351807 A1*  12/2015  Jackson ............... A61B 17/702
                                                        606/277

* cited by examiner

ANGLED OFFSET TULIP ASSEMBLY

TECHNICAL FIELD

The present invention relates to an improved implant device for use in spinal surgical procedures most particularly, an improved tulip design.

BACKGROUND OF THE INVENTION

Bone anchor screws come in a variety of shapes and sizes. One of the more common styles has a polyaxial head that allows for the screw to enter the bone structure at an ideal or preferred inclination. To achieve this polyaxial inclination, the head has a shape configured to rotate about its lower external surface. This lower surface can be one of a number of shapes like conical or spherical or hemispherical. This ability is often used in devices having a modular head assembly.

The pedicle screw assembly generally includes a tulip. A tulip is a body structure having two opposing sides spaced by a slotted opening to receive a spinal rod. The tulip often employs internal threads to receive a rod locking set screw to anchor or fix the rod in the tulip. The lower portion of the tulip has an opening to receive the pedicle screw in a base seat. Often, the tulip can have a saddle that both supports the rod along an underside of the rod. The saddle having an upper recessed curvature into which the rod sits and a lower cup like opening to receive the top of the pedicle screw head. When the saddle and rod and set screw are tightened, the screw angle is fixed against the tulip seat.

Often, it is preferred that the pedicle screw is first placed securely in the bone structure leaving the head protruding above the bone surface. In this surgical procedure the tulip assembly must be adapted to fit down onto the projecting screw head. To accomplish this, the surgeon must push the tulip onto and over the screw head without a clear path of vision. Accordingly, the placement must be accomplished without any way of knowing if the tulip or other device is properly secured. Thereafter, the device is tightened to complete the assembly and the only way to insure the assembly is secure requires an upward pulling of the tightened assembly. This works well when fixation of two adjacent vertebrae is being performed and the length of the fixation rod is relatively short.

If, however, the preferred spine screw bon fixation location is located where the vertebrae segments being fixed are not aligned to either vertically or laterally clear bone or previously installed implants, this often requires the use of a bent rod or requires the surgeon to bend the rod to custom fit the patient.

The present invention solves this problem in a unique one piece structure that allows a straight rod to be used in a tulip that is particularly crafted to accommodate an inclined and offset fixation to bone employing a single pedicle screw in the assembly.

SUMMARY OF THE INVENTION

An angled offset tulip has an angled offset tulip. The angled offset tulip has a bone screw receiving portion with a distal opening on a distal end and a rod receiving portion positioned offset a distance from a center of the distal opening and elevated above the distal opening to form an angle θ. The angle θ is defined as a line passing through the center of the distal opening and a slotted end center. θ is in the range of 5 degrees to less than 90 degrees, preferably 10 degrees to 60 degrees, more preferably 30 degrees to 60 degrees. The rod receiving portion has a slotted opening defined by a pair of sides, each side having a proximal end with threads for engaging a set screw to secure a rod. The angled offset tulip can be part of an angled offset tulip assembly also having a collet for receiving the head of a bone screw. The collet is positioned inside a recess of the bone screw receiving portion of the angled offset tulip. The collet is configured to fit over and receive and hold the head of the bone screw allowing the angled offset tulip to be of a modular construction. The angled offset tulip assembly may further include a bone screw.

The bone screw preferably has at least a partially hemispherical head allowing for a polyaxial alignment. The bone screw has one of the following head shapes; at least partially a hemispherical or spherical head, or any other bulbous head. The angled offset tulip is a single piece structure. The head of the bone screw has a driving feature for torsionally driving the screw into bone. The bone screw receiving portion of the angled offset tulip has a proximal end with a threaded proximal opening for receiving a set screw and a distal end with a distal opening for receiving a bone screw driver device.

In one embodiment, the angled offset tulip assembly further may have a collet being internal of the bone screw receiving portion, the collet having a distal end for receiving the bone screw. The collet has an exterior surface positioned between the proximal and distal ends. The exterior surface is sized to move axially inside the bone screw receiving portion aligned by a pair of complimentary convex arcuate projections. Each projection is configured to enter one of a pair of opposing slots in the recess. The collet has a plurality of arcuate fingers positioned to create a bulbous exterior shape with an interior receiving chamber complimentarily shaped relative to the head of the bone screw. The arcuate fingers are separated by slots extending from near the proximal end through the distal end in an initial pre-loaded position. The plurality of arcuate fingers collectively are larger in diameter than the tapered end annular opening of the distal end of the bone screw receiving portion. Upon insertion of the angled offset tulip, the bone screw receiving portion moves over the head of the bone screw. The collet moves proximally over the head simultaneously causing the arcuate fingers to flex and move past a maximum diameter of the head holding the head in the complimentary shaped interior bone screw receiving chamber. Upon tightening a set screw above the collet into a threaded opening of the bone receiving portion, the plurality of arcuate fingers are compressed about the head of the bone screw by the distal tapered end thereby fixing the bone screw inclination securely into the angled offset tulip. The collet has each finger having an arcuate shape with an inwardly positioned chamfered end for sliding on the surface of the head of the bone screw thereby flexing the plurality of arcuate fingers. The bone screw receiving portion has a conical surface tapering inward distally, the conical surface compresses the plurality of arcuate fingers when tightening the set screw. The relaxed outer diameter of the bulbous exterior of the collet is larger than a distal opening of the bone screw receiving portion. The collet has at least six or more fingers separated by slots. An inner surface of the collet along an inner surface of the plurality of fingers forms the complimentary head receiving chamber in a hemispherical or at least partial hemispherical shape sized to pass over and past the maximum diameter of the head of the bone screw. Each finger has a length, width or thickness sufficiently compliant to flexure or deflect inward or outward to expand or contract upon assembly and tightening.

A method of assembling an angled offset tulip assembly has the step of providing an angled offset tulip assembly having a rod receiving portion and a bone screw receiving portion; and positioning a collet inside the bone screw receiving portion. The method of assembling an angled offset tulip assembly also includes the step of positioning the collet inside the tulip to flex or deflect to an expanded condition as positioned over the head of a bone screw. The method of assembling an angled offset tulip assembly also includes the steps of installing a rod in said rod receiving portion and securing with a set screw.

BRIEF DESCRIPTION OF THE DRAWINGS

The invention will be described by way of example and with reference to the accompanying drawings in which.

DETAILED DESCRIPTION OF THE INVENTION

Figure 3:
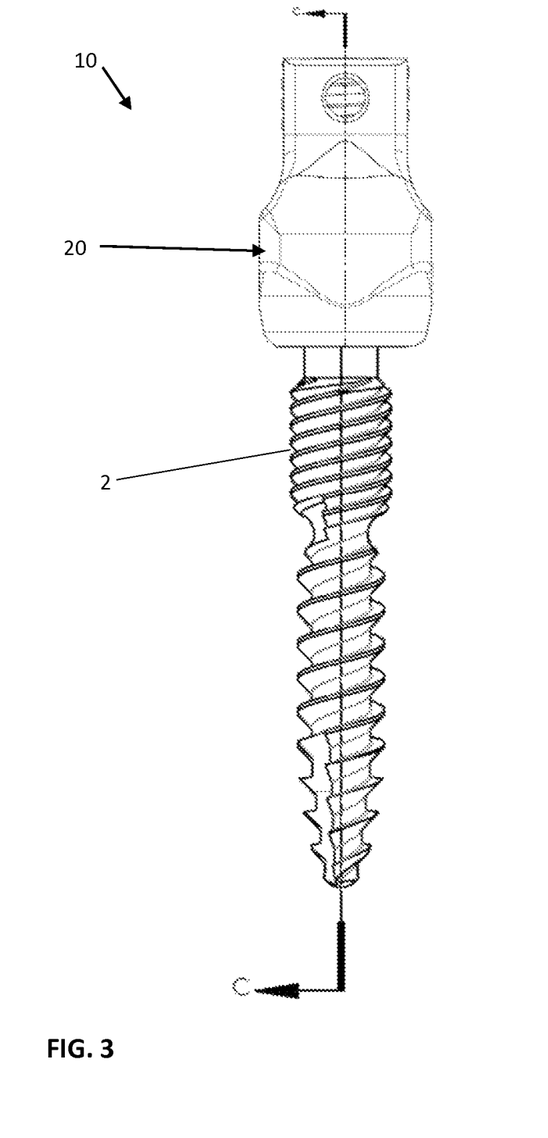
FIG. 3 is a side end plan view of the assembly of FIG. 2.
Figure 4:
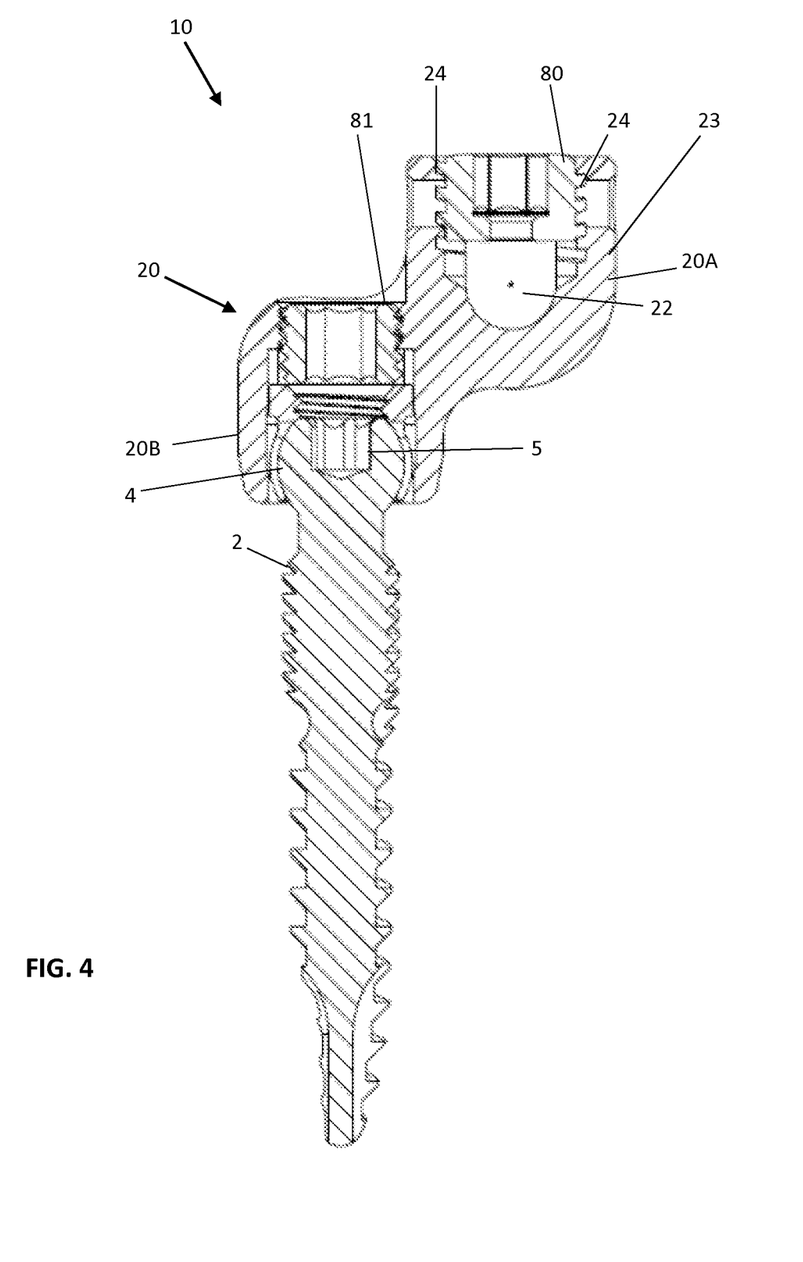
FIG. 4 is a cross sectional view of the assembly taken along lines C-C of FIG. 3.
Figure 5:
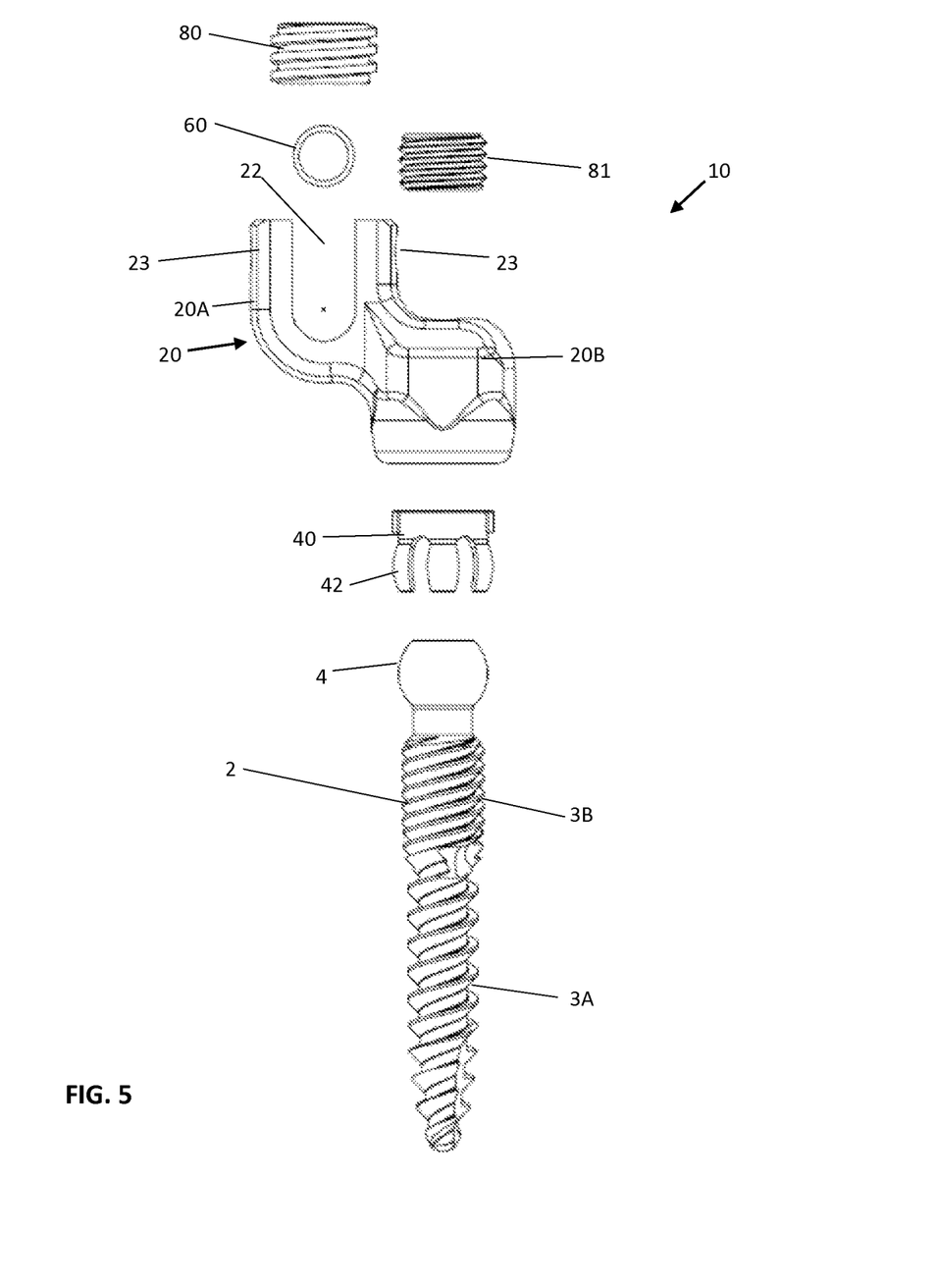
FIG. 5 is an exploded view of the angled offset tulip assembly.

With reference to FIGS. 1-5, various views of the angled offset tulip assembly 10 are shown with some of the views illustrating a collet 40, set screws 80, 81, a rod 60 and a bone screw 2 to complete the assembly. The angled offset tulip 20 as a single component is shown in FIGS. 6A-6D. FIG. 5 illustrates an exploded view of all of the components of the angled offset tulip assembly 10.

Figure 1:
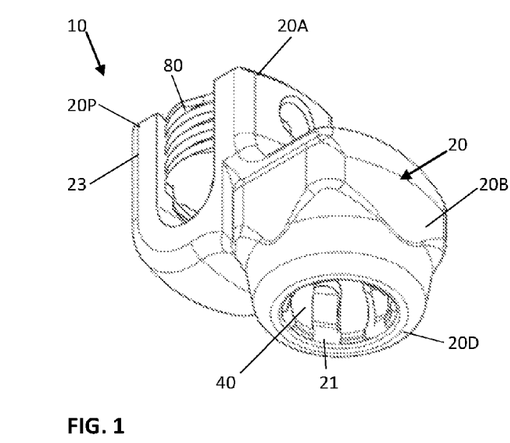
FIG. 1 is a perspective view of one embodiment of the present invention shown as an assembly with an angled offset tulip, a set screw and a bone screw receiving collet.
Figure 1A:
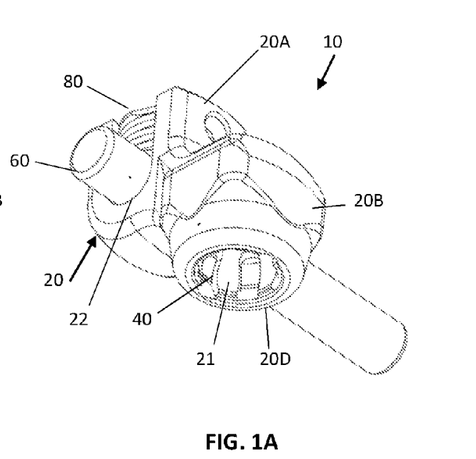
FIG. 1A is the tulip assembly with a rod shown fixed in the tulip or rod receiving slot.
Figure 2:
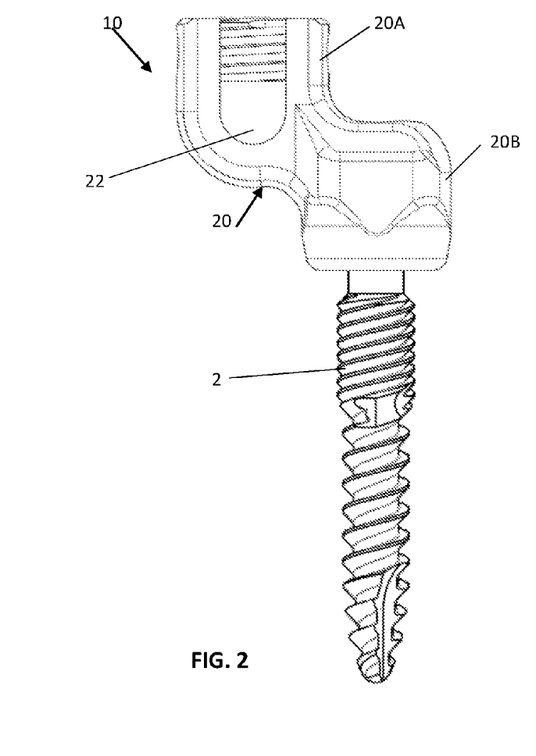
FIG. 2 is a front plan view of the assembly of FIG. 1 shown with a bone screw attached.

With reference to FIG. 1, the angled offset tulip 10 is shown in the lower perspective view looking upward to the assembly. As illustrated, the angled offset tulip 20 has two main portions, the rod receiving portion 20A and the bone screw receiving portion 20B. In the bottom of the bone screw receiving portion 20B an exemplary collet 40 is shown housed in a recess or receiving chamber 21 at a distal end opening 20D. Opposite the bone screw receiving portion 20B is a rod receiving portion 20A. The rod receiving portion 20A has a pair of sides 23 and a proximal end 20P. Interposed between the sides 23 is illustrated a set screw 80, the set screw 80 is configured to hold and tighten a rod 60. This is illustrated in FIG. 1A where the set screw 80 is shown clamping the rod 60 into a slotted opening 22 of the rod receiving portion 20A. With reference to FIG. 2, a bone screw 2 is shown inserted into the distal opening recess 21 and received by the collet 40.

FIG. 3 shows the bone screw 2 in a side end view showing the compact nature of the angled offset tulip assembly 10 when a bone screw 2 is housed therein.

FIG. 4 is a cross sectional view of the angled offset tulip assembly 10 taken along the lines C-C of FIG. 3. The angled offset tulip assembly 10 as shown has the rod receiving portion 20A slotted opening 22 with a threaded set screw 80 shown installed into the threads 24 of the rod receiving portion 20A along each side 23. As shown in this cross sectional view, the bone screw 2 with head 4 is received in the collet 40 in the recess 21 of the bone screw receiving portion 20B. The bone screw 2 has a screw driver receiving concavity or opening 5. This screw driver receiving opening 5 is designed to allow the bone screw 2 to be inserted into bone and firmly secured. This can occur with the set screw 81 removed allowing the driver tool and the angled offset tulip assembly 10 to be received into and fixed to a bone simultaneously. Alternatively, the construction of the angled offset tulip assembly 10 is configured so the bone screw 2 can be pre-assembled into the bone structure and then the angled offset tulip assembly 10 can be snapped over the head 4 of the bone screw 2 by aligning the distal opening 20D of the bone screw receiving portion 20B with the head 4 of the bone screw 2 and pressing the assembly firmly pushing the collet 40 over the head 4.

With reference to FIG. 5, an exploded view of the assembly 10 is illustrated. In FIG. 5, the bone screw 2 is shown having dual threads 3A, 3B; an initial bone entry thread 3A that transitions into a cortical bone thread 3B; when the bone screw 2 is fully seated into the bone structure leaving the screw head 4 which is partially hemispherical exposed. This hemispherical or partially hemispherical head 4 allows for polyaxial movement of the bone screw 2 when received in the collet 40 shown above the head 4 of the bone screw 2. The bone screw 2 on entry flexes fingers 42 on the collet 40 to allow it to be received. The angled offset tulip 20, as illustrated, has sides 23 on the rod receiving portion 20A. The bone screw receiving portion 20B has a distal opening for receiving the collet 40 and the bone screw 2. Directly above the rod receiving portion 20A and slotted opening 22 is illustrated a rod 60. This is a fixation rod that can be used in a procedure where vertebral bodies are being aligned and fixed during a surgical repair. This rod 60 can be straight, as illustrated, or can be bent or curved depending on the procedure being performed. Directly above the bone receiving portion 20B is a set screw 81. This set screw 81 is designed to engage threads in the bone receiving portion 20B and upon tightening will press the collet 40 into a position that locks the fingers 42 about the head 4 fixing the angulation and locking the tulip assembly 10 onto the bone screw 2. Similarly, on the opposite side, the internal threads 24 on the sides 23 of the rod receiving portion 20A allow the rod 60 to be placed fully into the slotted opening 22 and the set screw 80 will be threaded into the angled offset tulip 20 to secure the rod 60 into position.

Figure 6A:
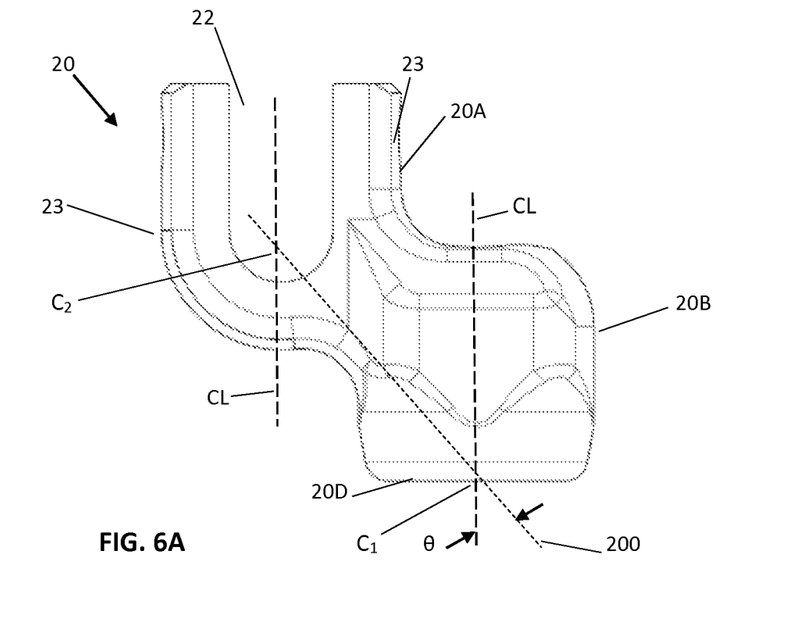
FIG. 6A is a side plan view of the angled offset tulip of the present invention.
Figure 6B:
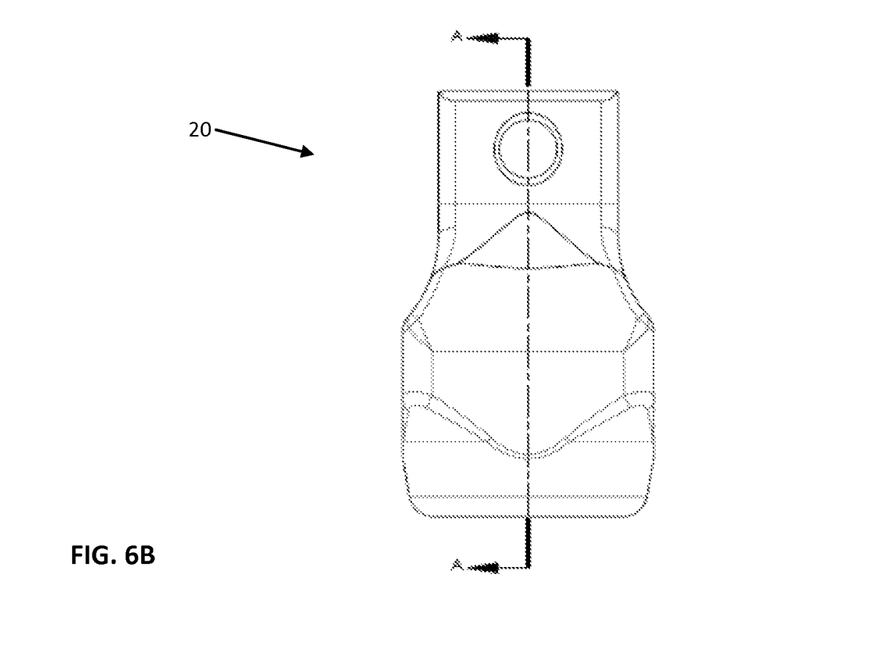
FIG. 6B is a side end plan view of the angled offset tulip.
Figure 6C:
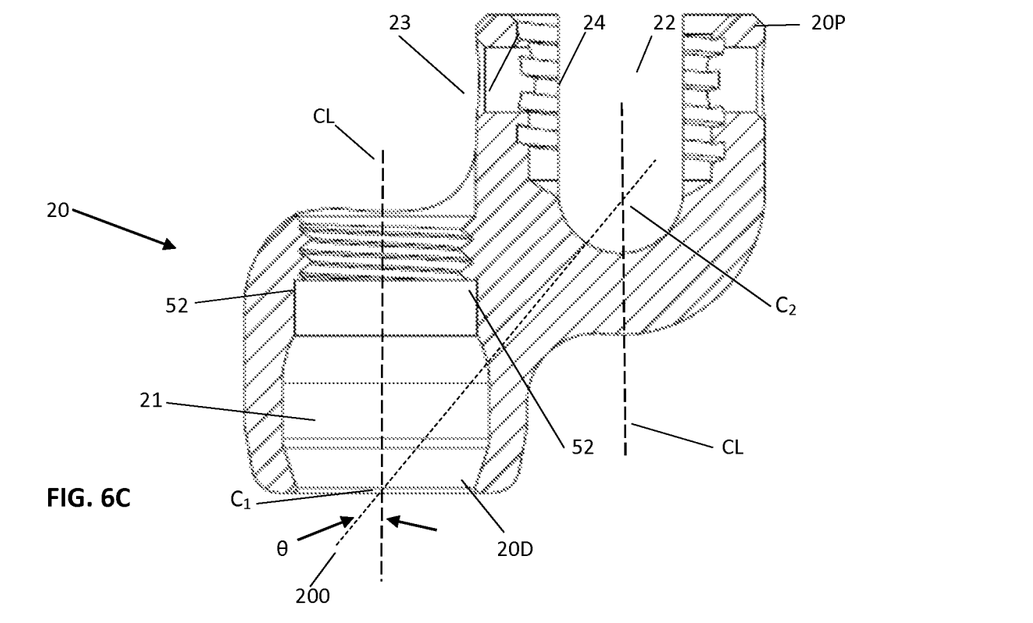
FIG. 6C is a cross sectional view taken along lines A-A of FIG. 6B.
Figure 6D:
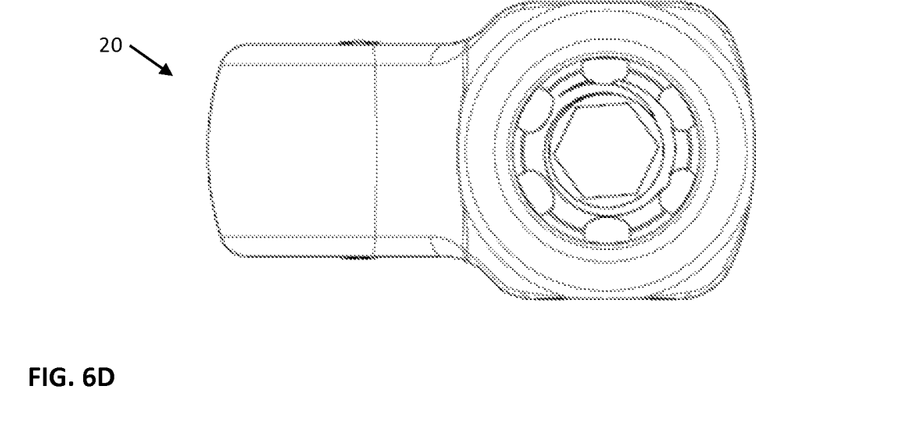
FIG. 6D is a bottom end view of the angled offset tulip.

With reference to FIGS. 6A-6D, the angled offset tulip 20 is illustrated as a single piece structure. The angled offset tulip 20 has a bone screw receiving portion 20B and a rod receiving portion 20A. As illustrated in FIGS. 6A and 6C, the bone screw receiving portion 20B has a distal opening 20D which has a center line CL passing through the center $C_1$ of the opening 20D. This center line CL is shown as dashed lines. The center line CL is offset laterally relative to the slotted opening 22 on the rod receiving portion 20A. The slotted opening 22 of the tulip has a semi-circular bottom that is also shifted angularly upward displacing it on an inclination relative to the distal opening 20D. A line 200 drawn through the center $C_1$ of the distal opening 20D for receiving a bone screw 2 and the center $C_2$ of the semi-circular bottom of the slotted opening 22 forms an angle θ relative to the center lines CL of the rod receiving portion 20A and the bone screw receiving portion 20B. The angle θ is in the range of 5 degrees to less than 90 degrees, preferably 10 degrees to 60 degrees, more preferably 30 degrees to 60 degrees. As illustrated, angle θ is shown at about 45 degrees. As it is important to note that the center $C_2$ of the semi-circular bottom opening forms an axis upon which the rod 60 when placed into the slotted opening 22 will be coaxially aligned, depending on the size of the rod 60 it will match or substantially match the arcuate circular opening. In such a fashion that the line 200 passing through the center lines CL will position the rod 60 slightly elevated and to one side of the bone screw 2. As illustrated, the center line CL of both portions 20A and 20B are parallel.

It is found that under certain procedures and anatomies that the bone screw 2 may be in such a position that when a prior art tulip is assembled to the head of a bone screw in a modular assembly, it may be difficult, if not impossible, to align a rod such that it can connect to another rod in an adjacent vertebrae due to bone or other physical structure impeding the rod's direct path to the next fixation point at the opposite end of the rod 60. Accordingly, by providing an angled offset tulip 20 with an inclination, this will enable the rod 60 to be shifted slightly, preferably bypassing any bone or structural impediments allowing for an easy fixation of the rod at the opposite end. The advantage of the present invention, when used with the collet 40 is that the bone screw 2 and collet 40 assembly, until tightened, are polyaxial and can move in any alignment rotationally about the axis of the bone screw or alternatively vertically up or down. This combination of mobility allows the offset angled tulip 20 to adjust its orientation upon assembly to assist the surgeon in properly positioning the bone screw 2 in the most ideal location and yet provide a tulip in a more optimum position than otherwise would be possible had the tulip been aligned with the axis of the bone screw 2.

Figure 7:
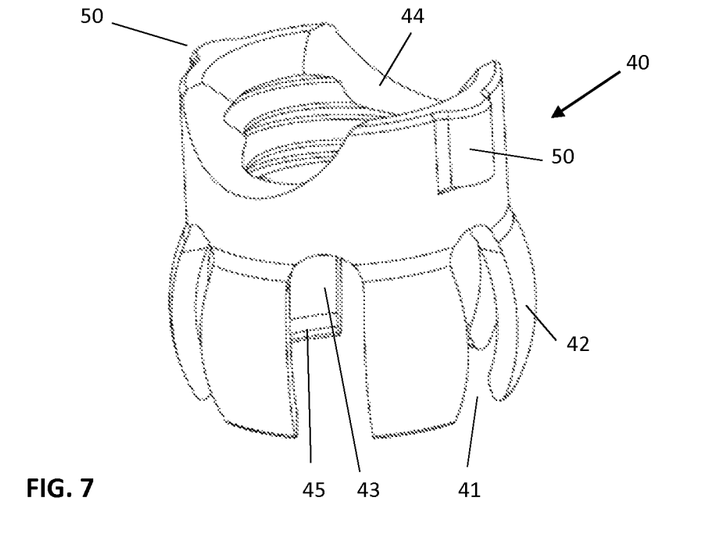
FIG. 7 is a perspective view of an exemplary collet that can be used with the present invention.

With reference to FIG. 7, an exemplary collet 40 is illustrated. The exemplary collet 40, as shown, has a pair of projections 50. These projections 50 are configured to enter into grooves 52 formed into the bone screw receiving portion of the tulip 20. Recesses or grooves 52 are cut into bone screw receiving portion 20B receiving chamber 21 allow the collet 40 to be positioned inside the receiving chamber 21 fixed angularly by the projections 50 and the complimentary grooves 52 such that the rotation of the collet 40 is prevented relative to the angled offset tulip 20. Therefore, the collet 40 when pressed into the distal opening 20D of the bone receiving portion 20B, will stay in position and not shift angularly nor will it be able to fall out of the assembly due to the flexure of the fingers 42. As illustrated the collet has a plurality of fingers 42 separated by slots 41. These fingers 42 are sufficiently elongated and bowed in such a fashion to create an exterior surface that fits within the interior surface of the receiving chamber 21. At a distal end of the collet a chamfer 45 is provided. This chamfer 45 facilitates the sliding of the fingers 42 onto the exterior surface of the bone screw 2 head 4 on assembly allowing the fingers 42 to flex outwardly. When this occurs, the collet 40 can shift upwardly in the receiving chamber 21 and allow the fingers 42 to bow outwardly sufficiently that the head 4 of the bone screw 2 will enter on assembly. This is true whether the bone screw 2 is pre-assembled to the angled offset tulip 20 or the bone screw 2 is already positioned in the bone and the angled offset tulip 20 is pressed onto the head 4 of the bone screw 2. The exemplary collet, as shown, is simply one version and some of the features such as the projections 50 with recesses 52 are optional.

As shown, the collet internal surface 43 is provided, it is complimentarily shaped to the head 4 of the bone screw 2 such that when the bone screw 2 is positioned into the collet 40, it will be held snugly, but with sufficient resistance that it cannot come apart easily, however, complete polyaxial movement is still maintained such that the bone screw 2 angularity can be adjusted as desired.

Figure 8:
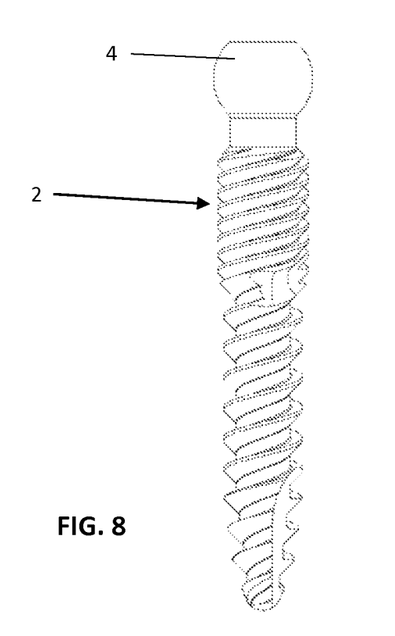
FIG. 8 is a perspective view of an exemplary pedicle or bone screw used with the present invention.

FIG. 8 shows an exemplary bone screw 2, as previously mentioned, with a partial or fully hemispherical head 4. As illustrated, the bone screw 2 has cutting flutes to allow for entry into the bone. The bone may be pre-drilled or the bone screw 2 can be of a self-tapping variety.

Figure 9:
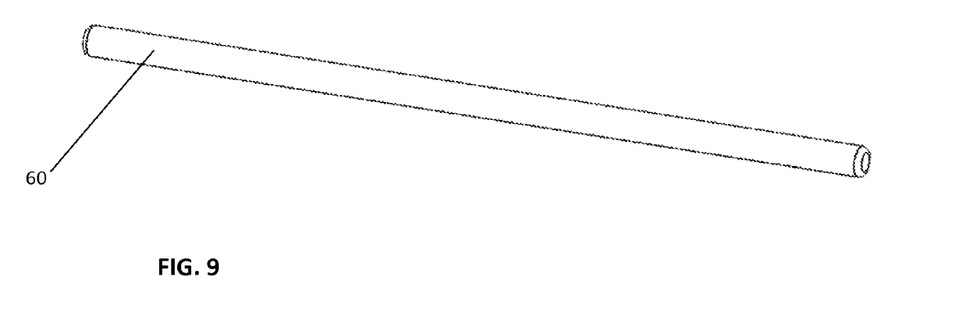
FIG. 9 is a view of the rod used with the present invention.

In addition, with reference to FIG. 9, an exemplary rod 60 is illustrated. The rod 60 is shown as a straight rod, however it can be curved or otherwise formed. Preferably, the exemplary rod 60 is sized to fit the slotted opening 22 on the rod receiving portion 20A of the angled offset tulip 20.

Figure 10:
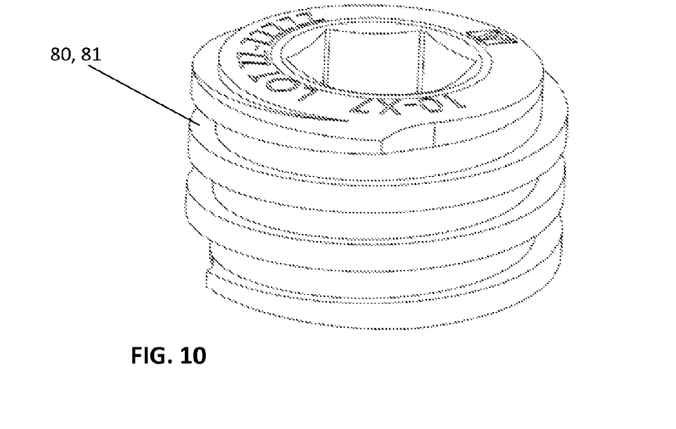
FIG. 10 is a view of the set screw used with the present invention.

FIG. 10 shows an exemplary set screw 80, 81. The exemplary set screws 80, 81 are virtually identical set screws that are configured to fit in the threaded portion of the rod receiving portion 20A and the threaded portion of the bone screw receiving portion 20B as shown in FIGS. 4 and 5.

Figure 11:
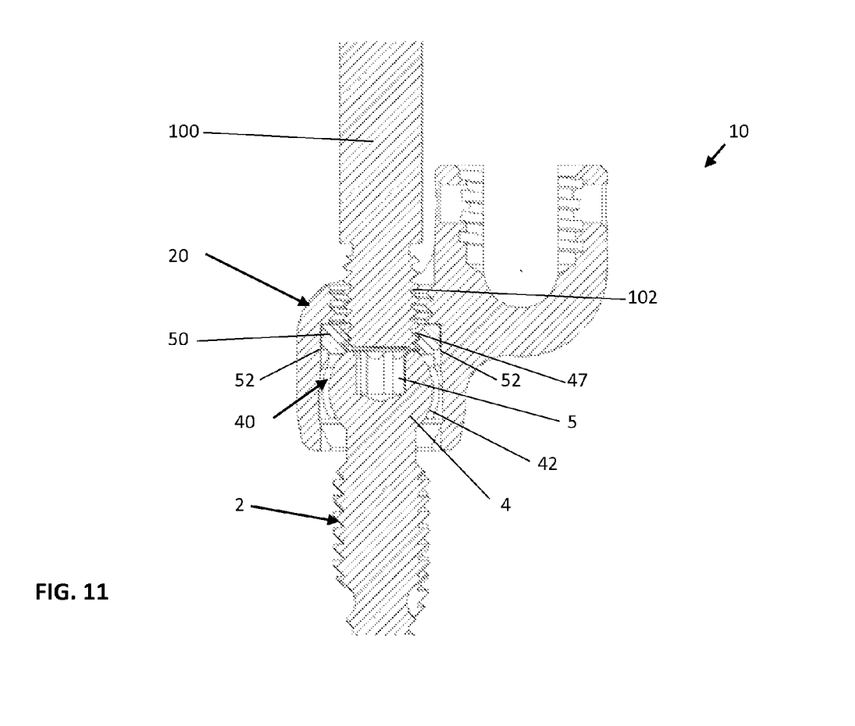
FIG. 11 shows how a release tool engages the collet of the present invention.
Figure 12:
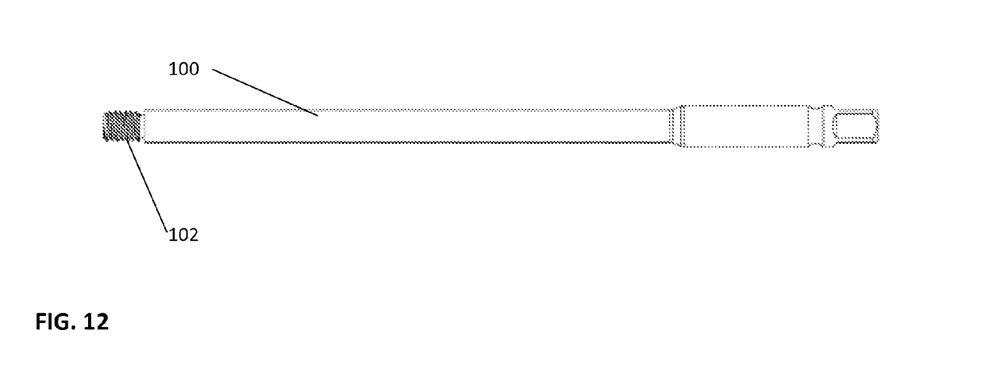
FIG. 12 shows a plan view of the release tool.

With reference to FIGS. 11 and 12, when the bone screw 2 has been fully inserted in the collet 40 and should the angled offset tulip 20 need to be released, the design is configured to allow a bone screw retrieval element to be threaded into the opening for receiving the set screw 81. When set screw 81 has been removed, this retrieval device 100 with threaded end 102 will threadingly engage the collet 40 through the threads 47 illustrated in FIG. 7. When the bone screw retrieval device 100 is threaded into the collet 40, it will push against the head 4 of the bone screw 2. By pulling the device 100 slightly into the receiving chamber 21, the fingers 42 are allowed to flex outwardly reversing the procedure that was used to install the head 4 of the bone screw 2 into the collet 40 in the first place. When this occurs, the flexure of the fingers 42 will be such that the head 4 of the bone screw 2 will be moved past the distal end of the fingers along the chamfers 45. This allows the head 4 of the bone screw 2 to pass as the tulip is being released from the head 4 of the bone screw 2. While it is unlikely that one would need to remove the tulip 20, this feature has been found beneficial in the event that the removal of the hardware is required after the surgical procedure.

As shown, the present invention can be sized to allow its use in various surgical procedures including the cervical and previous thoracic, lumbar, sacral, and iliac applications. In the cervical spine, the bone screws are not called bone or pedicle screws, but instead are commonly called lateral mass screws. Regardless of the nomenclature of this threaded fastener, as used herein the specification the screws have been generically called "bone screws", be they pedicle or otherwise. The offset tulip, as illustrated, has applications for all these procedures. The offset tulip 20 is especially useful in the iliac connection and therefore provides an opportunity to improve this procedure. The device is exemplary with the drawings illustrating exemplary embodiments, it is understood that alternative embodiments may be employed. For example, as illustrated in FIG. 4, the collet 40 has a flat or top end on the bone screw receiving portion 20B, this is further illustrated in FIG. 5 of the exploded view. However, in FIG. 7, the exemplary collet 40, which is otherwise identical to that shown in FIGS. 4 and 5, has the slotted concave region 44. This slotted concavity 44 as shown is provided due to the fact that this collet 40 can be universally used in a more conventional tulip to make a modular assembly or in other tulip designs. Accordingly, the collet 40 may have this concavity 44 or may be flat as shown in FIGS. 4 and 5. The concavity 44 creates a saddle portion into which the rod 60 can complimentarily fit when the collet is used on the rod receiving portion 20A of the device.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An angled offset tulip assembly comprising:
    an angled offset tulip, the angled offset tulip being a single one-piece component having a rod receiving portion and a bone screw receiving portion, the bone screw receiving portion has a distal opening on a distal end and a threaded opening on a proximal end and the rod receiving portion is positioned offset a distance from a center of the distal opening and elevated above the distal opening to form an angle θ, θ being defined as a line passing through the center of the distal opening and a slotted end center, θ being in the range of 30 degrees to less than 60 degrees, the rod receiving portion having a slotted opening defined by a pair of sides, each side having a proximal end with threads for engaging a first set screw to secure a rod;
    a collet for receiving a head of the bone screw, the collet having a proximal end and a distal end, the collet being inside a recess of the bone screw receiving portion, and wherein the collet is configured to fit over and receive and hold the head of the bone screw; and
    wherein the collet has an exterior surface positioned between the proximal and distal ends, the exterior surface being sized to move axially inside the tulip aligned by a pair of complimentary convex arcuate projections, each projection configured to enter an opposing slot in the recess, the collet having a plurality of arcuate fingers positioned to create a bulbous exterior shape with an interior receiving chamber complimentarily shaped relative to the head of the bone screw, the arcuate fingers separated by slots extending from near the proximal end through the distal end in an initial pre-loaded position, the plurality of arcuate fingers collectively being larger in diameter than a tapered end annular opening at the distal opening of the tulip; and
    wherein upon insertion of the bone screw receiving portion of the tulip over the head of the bone screw, the collet moves proximally over the head simultaneously causing the arcuate fingers to flex and move past a maximum diameter of the head of the bone screw, loosely holding the head in the complimentary shaped interior receiving chamber allowing polyaxial movement of the angled offset tulip to adjust the orientation of the rod receiving portion and upon tightening of a second set screw in the threaded opening on the proximal end of the bone screw receiving portion, the plurality of arcuate fingers are compressed about the head of the bone screw by the tapered end annular opening at the distal opening thereby fixing the bone screw into the tulip and the orientation of the rod receiving portion prior to tightening the first set screw against the rod to be secured in the rod receiving portion.

2. The angled offset tulip assembly of claim 1 further comprises:
    a bone screw.

3. The angled offset tulip assembly of claim 2 wherein the bone screw has at least a partially hemispherical head with an end configured to receive a bone screw driver device.

4. The angled offset tulip assembly of claim 2 wherein the bone screw has at least a partially hemispherical head.

5. The angled offset tulip assembly of claim 2 wherein the bone screw has one of the following head shapes; at least partially a hemispherical or spherical head.

6. The angled offset tulip assembly of claim 1 wherein the bone screw receiving portion of the angled offset tulip has a proximal end with a threaded proximal opening for receiving the second set screw, the second set screw having an opening for receiving a driver device.

7. The angled offset tulip assembly of claim 1 wherein the slotted opening of the rod receiving portion of the angled offset tulip has a circular bottom to receive a rod being vertically elevated relative to the distal opening for receiving a bone screw.

8. The angled offset tulip assembly of claim 7 wherein the slotted opening is offset relative to the distal opening, the slotted opening having a center plane passing through an axis of the circular bottom, the rod receiving portion having a center plane being parallel relative to a distal opening center plane passing through the center of the distal opening of the bone screw receiving portion.

9. The angled offset tulip assembly of claim 1 wherein a bottom of the rod receiving portion is positioned above the distal end of the bone screw receiving portion.

10. The angled offset tulip assembly of claim 1 wherein the collet has each finger having an arcuate shape with an inwardly positioned chamfered end for sliding on the surface of the head of the bone screw thereby flexing the plurality of arcuate fingers.

11. The angled offset tulip assembly of claim 1 wherein the recess of the tulip has a conical surface tapering inward distally, the conical surface compresses the plurality of arcuate fingers of the collet when tightening the second set screw.

12. The angled offset tulip assembly of claim 1 wherein the relaxed outer diameter of the bulbous exterior of the collet is larger than the distal opening of the tulip.

13. The angled offset tulip assembly of claim 1 wherein the collet has at least six or more fingers separated by slots.

14. The angled offset tulip assembly of claim 13 wherein an inner surface of the collet along an inner surface of the plurality of fingers forms the complimentary head receiving chamber in a hemispherical or at least partial hemispherical shape sized to pass over and past the maximum diameter of the head of the bone screw.

15. The angled offset tulip assembly of claim 14 wherein the head of the bone screw has a driving feature for torsionally driving the screw into bone.

16. The angled offset tulip assembly of claim 1 wherein each finger has a length, width or thickness sufficiently compliant to flexure or deflect inward or outward to expand or contract upon assembly and tightening of the second set screw.

17. A method of assembling an angled offset tulip assembly comprises the step of:

providing an angled offset tulip assembly, including a single one piece angled offset tulip having a bone screw receiving portion and an angled offset tulip rod receiving portion offset from the bone screw receiving portion, the angled offset tulip having a bone screw receiving portion with a distal opening on a distal end and the rod receiving portion positioned offset a distance from a center of the distal opening and elevated above the distal opening to form an angle θ, θ being defined as a line passing through the center of the distal opening and a slotted end center, θ being in the range of 30 degrees to less than 60 degrees, the rod receiving portion having a slotted opening defined by a pair of sides, each side having a proximal end with threads for engaging a set screw to secure a rod; and positioning a collet inside a recess of the bone screw receiving portion of the angled offset tulip, the collet being retained in the recess, the collet having an exterior surface positioned between the proximal and distal ends, the exterior surface being sized to move axially inside the tulip aligned by a pair of complimentary convex arcuate projections, each projection configured to enter an opposing slot in the recess, the collet having a plurality of arcuate fingers positioned to create a bulbous exterior shape with an interior receiving chamber complimentarily shaped relative to the head of the bone screw, the arcuate fingers separated by slots extending from near the proximal end through the distal end in an initial pre-loaded position, the plurality of arcuate fingers collectively being larger in diameter than a tapered end annular opening at the distal opening of the tulip; and wherein upon insertion of the bone screw receiving portion of the angled offset tulip over the head of the bone screw, the collet moves proximally over the head simultaneously causing the arcuate fingers to flex and move past a maximum diameter of the head holding the head in the complimentary shaped interior receiving chamber and upon tightening a second set screw, the plurality of arcuate fingers are compressed about the head of the bone screw by the tapered end annular opening at the distal opening thereby fixing the bone screw into the tulip.

18. The method of assembling an angled offset tulip assembly of claim 17 also includes the step of positioning the collet inside the tulip to flex or deflect to an expanded condition as positioned over the head of a bone screw.

19. The method of assembling an angled offset tulip assembly of claim 18 also includes the steps of installing a rod in said angled offset tulip rod receiving portion and securing with a first set screw, and after adjusting and fixing a bone screw angle or inclination as the second set screw in said bone screw receiving portion moves the collet to a tightened position against the bone screw head.

* * * * *